US005745019A

United States Patent [19]
Renger

[11] Patent Number: 5,745,019
[45] Date of Patent: Apr. 28, 1998

[54] MAGNETIC ANNUNCIATOR

[75] Inventor: Herman Lee Renger, Calabasa, Calif.

[73] Assignee: Pacesetter, Inc., Sylmar, Calif.

[21] Appl. No.: 648,748

[22] Filed: May 16, 1996

[51] Int. Cl.⁶ .................................................. H01F 7/08
[52] U.S. Cl. .................................................. 335/222; 335/229
[58] Field of Search .......................... 335/222, 229-234;
340/384.1-404.3; 607/4-7, 14, 27, 32, 33;
318/128; 310/12-15, 127; 381/199-201

[56] References Cited

U.S. PATENT DOCUMENTS

| | | | |
|---|---|---|---|
| 3,319,201 | 5/1967 | Coen | 381/199 |
| 3,783,877 | 1/1974 | Bowers | 128/419 P |
| 3,886,419 | 5/1975 | Omura et al. | 318/132 |
| 3,965,377 | 6/1976 | Carbonneau | 310/12 |
| 4,086,916 | 5/1978 | Freeman et al. | 128/2.05 T |
| 4,088,139 | 5/1978 | Auerbach | 128/419 PT |
| 4,102,346 | 7/1978 | Fulker | 128/419 PS |
| 4,210,149 | 7/1980 | Heilman et al. | 128/419 D |
| 4,295,474 | 10/1981 | Fischell | 128/697 |
| 4,345,603 | 8/1982 | Schulman | 128/419 PT |
| 4,407,289 | 10/1983 | Nappholz et al. | 128/419 PG |
| 4,494,022 | 1/1985 | Kawara et al. | 310/14 |
| 4,649,359 | 3/1987 | Doki et al. | 335/222 |
| 5,190,034 | 3/1993 | Sholder | 128/419 PG |
| 5,624,376 | 4/1997 | Ball et al. | 600/25 |

Primary Examiner—Michael L. Gellner
Assistant Examiner—Raymond Barrera

[57] ABSTRACT

An annunciator is provided for an organ stimulating system which is implantable in the body of a patient. A tubular support member is mounted at one end on the casing for the organ stimulating system and extends to a free end and an electrically conductive coil encircles the support member. An elongated oscillating member includes a field return member of magnetically permeable material which is spaced from and generally encircles the support member. The field return member extends between an integral head member at a proximal end generally proximate the free end of the support member and a distal end generally proximate the casing. A stack member is mounted on the head member and extends away therefrom toward the casing for the organ stimulating system. The stack member has an outer peripheral surface which is spaced from the support member and includes a magnetically permeable pole piece and a permanent magnet member, the pole piece and the magnet member being in stacked relationship which together produce a radial magnetic field which extends through the coil and to the field return member. A resilient member intermediate the stack member and the casing of the organ stimulating system biases the oscillating member to an initial position. With this construction, cyclic energization of the coil interacts with the radial magnetic field to cause the oscillating member to oscillate relative to the initial position. A similarly constructed activity sensor is also disclosed for relating patient movement.

9 Claims, 3 Drawing Sheets

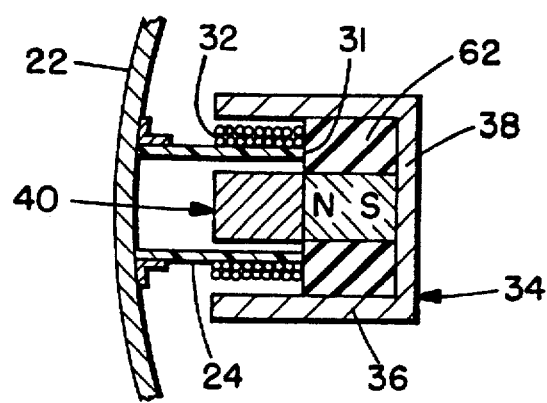
FIG. 5.
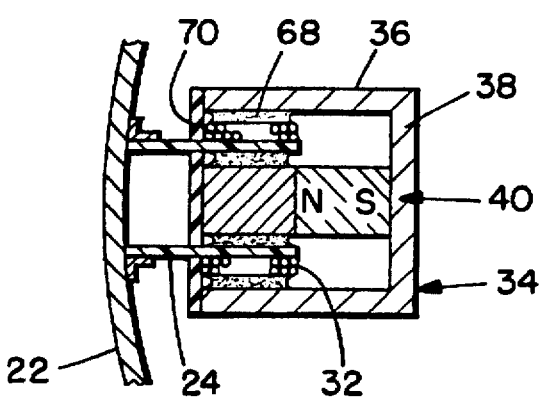
FIG. 8.
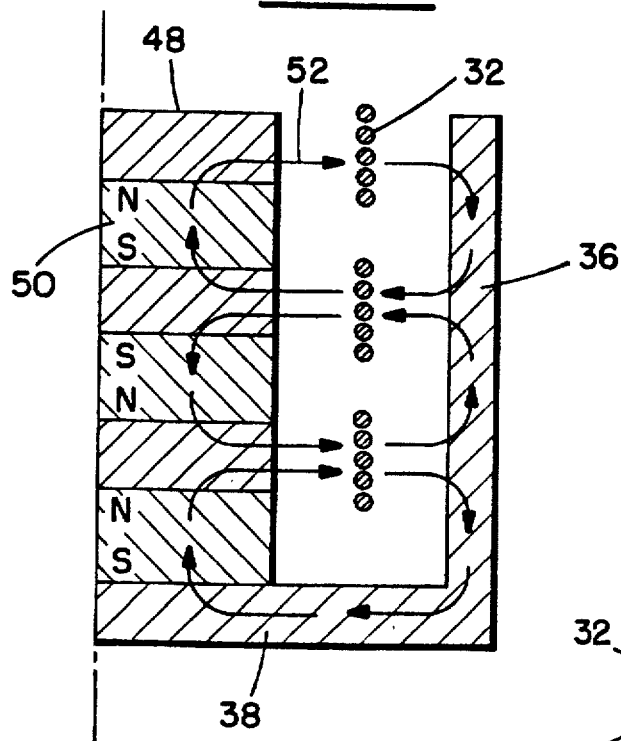
FIG. 2.
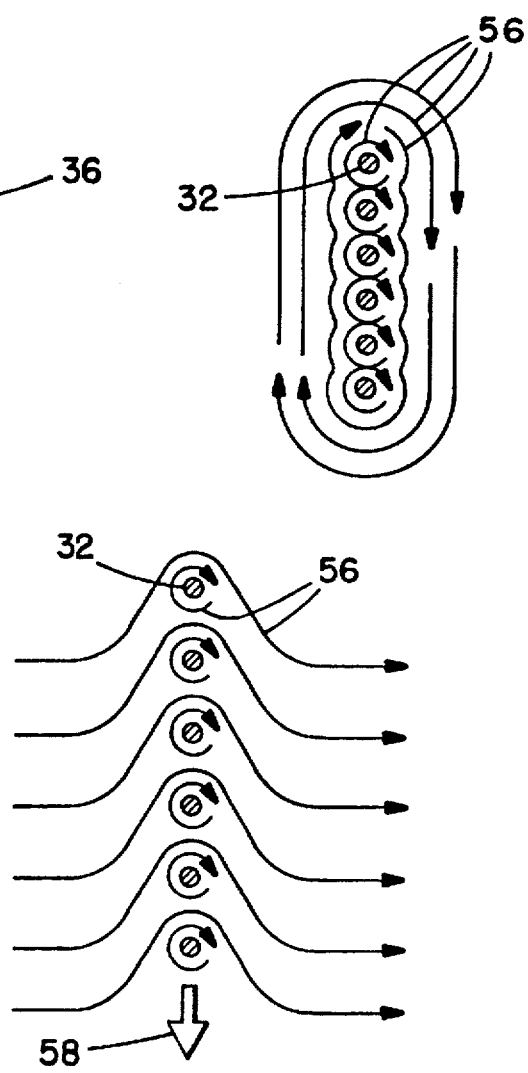
FIG. 3.
FIG. 4.

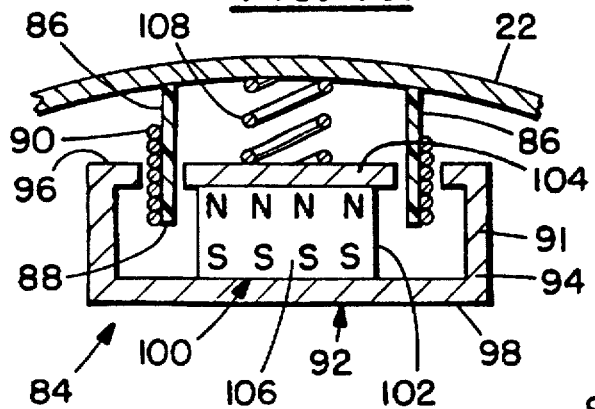
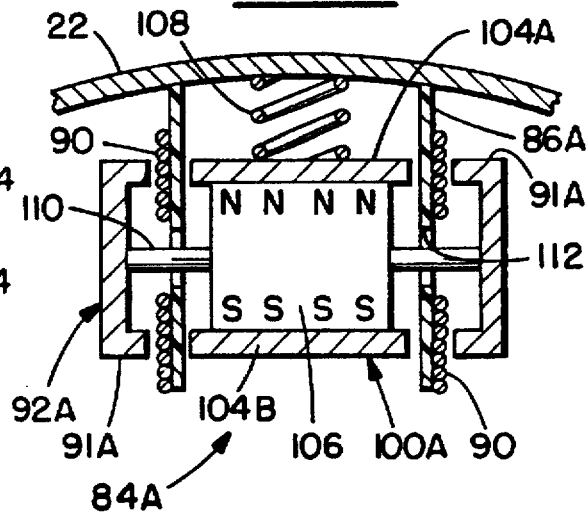
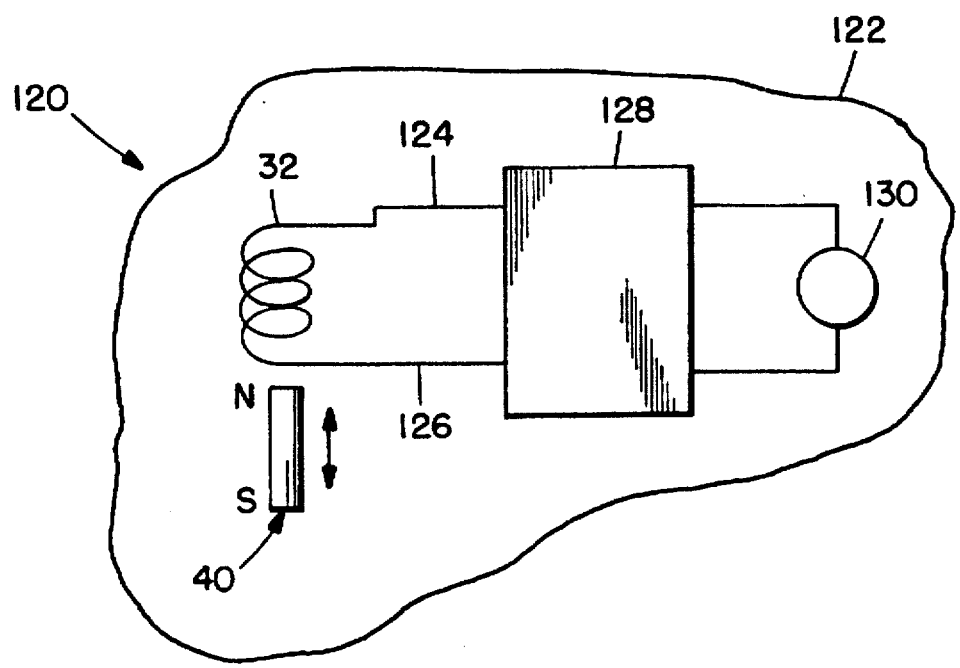

MAGNETIC ANNUNCIATOR

FIELD OF THE INVENTION

The present invention relates to annunciator devices for organ stimulating systems implantable in the body of a patient and in particular to such devices which may be used in combination with implantable defibrillator systems, for example, and be assured of attracting the attention of the patient upon the occurrence of a predetermined event.

BACKGROUND OF THE INVENTION

Implantable defibrillation systems are known in the art which deliver a high-voltage defibrillation pulse to the heart when the onset of fibrillation is detected and/or in the event of a detected complete loss of cardiac output. Such known devices are also capable, if the heart exhibits an arrhythmia such as atrial fibrillation, atrial flutter or tachycardia, or ventricular tachycardia, of cardioverting the heart by delivering a low-voltage pulse in an attempt to regain synchronous operation of the heart, instead of delivering the high voltage defibrillation pulse. In known devices of this type, considerable effort has been devoted to the development of detection circuitry to accurately identify heart arrhythmias which require defibrillation or cardioversion (i.e., insuring true-positives) and for preventing a "no output" situation when an output is actually needed (i.e., preventing true-negatives). Steps have also been taken to prevent the delivery of a defibrillation or cardioversion pulse when none is needed (i.e., preventing false-positives). See, for example, commonly assigned U.S. Pat. No. 5,190,034 to Sholder.

It is important to provide a safety mechanism for preventing implantable systems of this type from releasing a treatment pulse when the patient feels no need for such a pulse. A false-positive output could result in severe discomfort to the patient, and may trigger ventricular tachycardia, ventricular fibrillation and ultimately death if the system cannot react quickly enough to provide proper treatment to revive the patient.

It is known from U.S. Pat. No. 4,086,916 to Freeman at al. to contain a cardiac monitoring system in a wristwatch worn by a patient, the system including circuitry for detecting an erratic heartbeat, a missing pulse or other irregularities and providing an alarm indication, audio and visual, when such an event is detected.

It is also known from U.S. Pat. No. 4,088,139 to Auerbach to provide, in an implantable cardiac pacing system, means for generating a marking pulse in the pacemaker monitoring system if an event such as loss of capture occurs. The patient is not immediately informed of the occurrence of such an event, however, the system is provided with telemetry means so that when the recorded data is subsequently read out and examined by a physician, the data will include the marker indicating that loss of capture has occurred. The physician can then take such corrective steps as may be necessary.

An implantable pacing system is disclosed in U.S. Pat. No. 4,102,346 to Fulker which includes an alarm device as part of the implanted unit which generates an alarm signal to inform the pacemaker user when the battery source of power of the pacemaker is nearing end of life or is malfunctioning.

An implantable tissue stimulating device is disclosed in U.S. Pat. No. 4,345,603 to Schulman which activates an alarm which informs the patient in whom the system is implanted that the battery is in need of replacement. After the user has been so informed, the user applies a magnet externally in the vicinity of the implanted unit to deactivate the monitoring system and thereby cease the continued operation of the alarm.

A pacemaker for controlling tachycardia is disclosed in U.S. Pat. No. 4,407,289 to Nappholz et al. also disclosing means for informing a pacemaker user of the remaining battery life. The user places a magnet externally in the vicinity of the implanted unit, which thereby causes the implanted unit to generate two pulses which can be seen on the patient's ECG waveform. The time separation between the two pulses indicates the remaining battery potential. Application of the magnet, after the pulses have been generated, temporarily disables the device.

In U.S. Pat. No. 5,190,034, noted earlier, an implantable arrhythmia treatment system is disclosed which includes reliable protection against the release of unneeded treatment pulses, that is, which provides protection against a false-positive output. The disclosed system utilizes an alarm generator which may be disposed in the implanted unit, or in an external unit. The alarm may be of any type which does not require constant, active monitoring by the user, such as a sensory alarm, for example, an audio alarm generator or a tactile alarm generator or "tickler".

Other examples of implantable arrhythmia devices which include an alarm generator, either audio, tactile, or visual, are found in U.S. Pat. Nos. 4,295,474 to Fischell; 4,210,149 to Heilman et al.; and 3,783,877 to Bowers.

According to the current state of the art, error conditions are typically announced within an implantable cardioverter defibrillator (ICD) using a piezo annunciator or beeper. The current Eagle Model 2800 in development by Pacesetter, Inc., A St. Jude Medical Company, Sylmar, Calif., utilizes a piezo actuator to flex the titanium can at audio frequencies. However, the efficacy of audio emissions from devices implanted abdominally can be questioned. The attenuation of the audio transmitted through tissue is dramatic. Aged patients commonly have hearing loss that further decreases their sensitivity to implanted audio generators.

It was in light of the foregoing that the present invention was conceived and has now been reduced to practice.

SUMMARY OF THE INVENTION

According to the invention, an annunciator is provided for an organ stimulating system which is implantable in the body of a patient. A tubular support member is mounted at one end on the casing for the organ stimulating system and extends to a free end and an electrically conductive coil encircles the support member. An elongated oscillating member includes a field return member of magnetically permeable material which is spaced from and generally encircles the support member. The field return member extends between an integral head member at a proximal end generally proximate the free end of the support member and a distal end generally proximate the casing. A stack member is mounted on the head member and extends away therefrom toward the casing for the organ stimulating system. The stack member has an outer peripheral surface which is spaced from the support member and includes a magnetically permeable pole piece and a permanent magnet member, the pole piece and the magnet member being in stacked relationship which together produce a radial magnetic field which extends through the coil and to the field return member. A resilient member intermediate the stack member and the casing of the organ stimulating system biases the oscillating member to an initial position. With this construction, cyclic energization of the coil interacts with the radial magnetic field to cause the oscillating member to oscillate relative to the initial position. A similarly constructed activity sensor is also disclosed for relating patient movement.

A primary object of the invention, therefore, is to produce an annunciator for an implanted pacemaker which produces vibration and possibly sound, one which utilizes low voltage and requires minimal space.

The device of the invention uses coils and a permanent magnet driven field structure to produce the forces and accelerations necessary to generate vibrations. In addition, it utilizes the sudden deceleration resulting when a relatively massive moving unit strikes a stop member to produce higher harmonics and sound. As implemented in one embodiment, this device uses multiple permanent magnets and multiple coil sections in order to obtain the greatest effect out of the space available.

Either pulsed DC or AC may be employed to drive the invention. A compression spring helps to position the magnetic structure with respect to the coils and makes the system mechanically resonant to improve efficiency.

Further expedients involve the use of magnetically permeable fluid or steel balls to support the magnetic structure and improve the magnetic circuits. Powerful magnetic fields may be utilized to keep the fluid or balls in place. Additionally, fluid on both the outside and inside of the magnetic structure may be used to help cool the coil.

An additional feature of the device described is that it can be used as an activity sensor. The moveable mass will be affected by acceleration or vibration of the patient and will generate a voltage on the terminals which can easily be monitored.

The present invention offers numerous advantages. It provides a compact structure while using a relatively massive magnetic structure as a moving part. It may use miniature balls or magnetically permeable fluid to center the interactive components, to strengthen the magnetic field and to cool the electrical coils. It can be made to hard limit to thereby produce mechanical shocks and sound.

In a first instance, it provides a novel annunciator device applicable to organ stimulating systems which are implantable in a patient's body. More particularly, the invention may be used in combination with implantable defibrillator systems, for example, and be assured of attracting the attention of the patient upon the occurrence of a predetermined event. Still more particularly, the invention may serve to produce a subaudible vibration which would be detectible by the sense of touch by a patient who may have experienced hearing loss. Alternatively, the invention may be operated to simultaneously produce an audible and a tactile vibration for use by a patient who may not have experienced undue hearing loss.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 2 is a diagrammatic side elevation view of a further modification of FIG. 1 illustrating a component of the annunciator including permanent magnets and depicting a resulting magnetic field;

FIG. 3 is a diagrammatic cross section view through an electrically conductive coil which is another component of the annunciator of FIG. 1 and depicting a resulting magnetic field when the coil is electrically energized;

FIG. 4 is a diagrammatic cross section view through the electrically conductive coil of FIG. 3 but illustrating an altered magnetic field which results when the magnetic field depicted in FIG. 2 interacts with the magnetic field of FIG. 3;

FIGS. 5-11 are all diagrammatic side elevation views, in section, of annunciators, generally similar to the annunciator of FIG. 1, but illustrating different embodiments of the invention; and FIG. 12 is a schematic diagram of a motion sensor for monitoring the movement of a patient and constructed in the manner of the annunciator illustrated in the preceding views.

DESCRIPTION OF THE PREFERRED EMBODIMENTS

Figure 1:
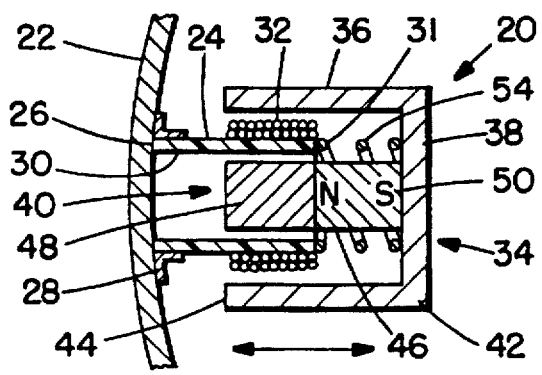
FIG. 1 is a diagrammatic side elevation view, in section, of an annunciator, embodying the present invention, for an organ stimulating system implantable in the body of a patient.

Turn now to the drawings and, initially, to FIG. 1 which diagrammatically illustrates an annunciator 20 embodying the present invention for an organ stimulating system encapsulated within a casing 22 and implantable in the body of a patient. The annunciator 20 comprises an elongated support member 24 which is suitably mounted at one end 26 on the casing 22 for the organ stimulating system. An annular collar 28 may further aid in mounting the end 26 to the casing 22. This may be achieved, for example, by welding, by use of glue, or by other appropriate joining expedient. The support member 24 is tubular, perhaps cylindrical, has an inner peripheral surface 30, extends to a free end 31, and is encircled by an electrically conductive coil 32. The coil may be bonded to the support member in any suitable manner to assure it will retain a desired position lengthwise of the support member.

The annunciator 20 also includes an elongated oscillating member 34 which, in turn, includes a field return member 36, a head member 38, and a stack member 40. The field return member 36 is comprised of magnetically permeable material and is spaced from and generally encircles the support member 24. The field return member 36 is tubular, perhaps cylindrical, and extends between a proximal end 42 generally proximate the free end 31 of the support member 24 and a distal end 44 generally proximate the casing 22. The head member 38 is integral with the field return member 36 and overlies its proximal end 42. The stack member 40 is mounted or bonded on the head member 38 in a suitable manner and extends away therefrom toward the casing 22 for the organ stimulating system. The stack member may extend generally parallel to, or be concentric with, the field return member 36. The stack member also has an outer peripheral surface 46 which is spaced from the inner peripheral surface 30 of the support member 24. The stack member includes a magnetically permeable pole piece 48 and a permanent magnet member 50 which are suitably bonded together and assume a stacked relationship. As seen in FIG. 2, as related to an embodiment to be described, the pole piece 48 and the permanent magnet member 50 operate together to produce a radial magnetic field, graphically represented by curved field lines 52, which extends through the coil 32 and to the field return member 36.

A resilient device, illustrated as a compression spring 54, is positioned intermediate, and bears against, respectively, the head member 38 and the free end 31 of the support member 24. With this construction, the spring 54 biases the oscillating member 34 to an initial position whereat the pole piece 48 is generally coextensive with the coil 32. Cyclic energization of the coil, either by means of AC or pulsed DC current, causes interaction with the radial magnetic field to cause the oscillating member 34 to oscillate relative to the initial position. FIG. 3 diagrammatically illustrates, by means of a plurality of successive outwardly expanding magnetic field lines 56, a magnetic field which occurs in the vicinity of the coil 32 when so energized. FIG. 4, in turn, depicts the result when the magnetic field produced by the oscillating member 34 interacts with the magnetic field surrounding the energized coil. Applying the customary right hand rule, the resultant is a force imparted to the coil 32 and its support member 24 in the direction of an arrow 58 and an equal and opposite reaction force is imparted to the oscillating member 34.

The components of the annunciator 20 may have a variety of different relative dimensions and still achieve the desired goal of creating noise and/or vibration. For example, viewing FIG. 1A, a modified annunciator 20A has a modified stack member 40A which extends to a base end 60 at its extremity. In this instance, when the modified oscillating member 34A assumes the initial position, both the base end 60 of the stack member 40A and the distal end 44A of the field return member 36A are spaced from the casing 22. However, cyclic energization of the coil 32 causes oscillation of the oscillating member 34A and results in the base end 60 alone striking the casing 22 with resultant vibration and production of sound.

Figure 1C:
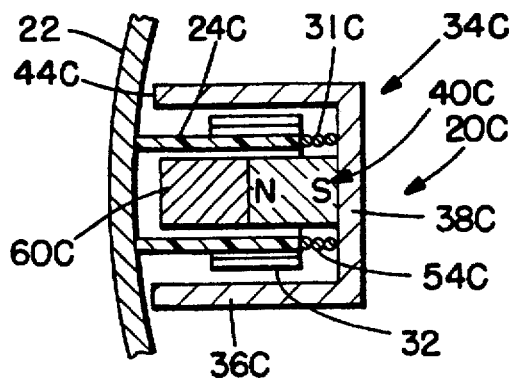
FIGS. 1A, 1B, and 1C are all diagrammatic side elevation views, in section, of annunciators, generally similar to the annunciator of FIG. 1, but illustrating different embodiments of the invention.
Figure 1A:
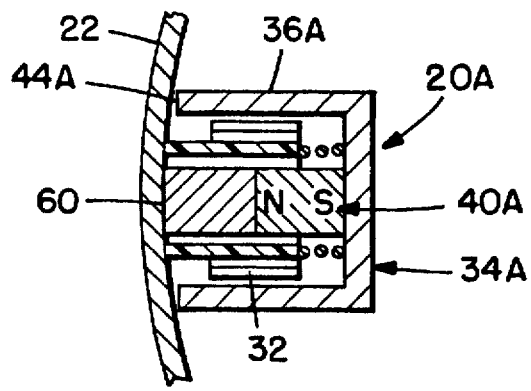
Figure 1B:
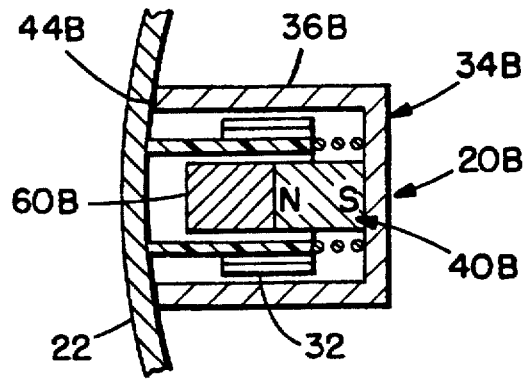

In another construction, viewing FIG. 1B, modified annunciator 20B has a modified field return member 36B which extends to a distal end 44B. In this instance, again, when the modified oscillating member 34B assumes the initial position, both the base end 60B of the stack member 40B and the distal end 44B of the field return member 36B are spaced from the casing 22. However, cyclic energization of the coil 32 causes oscillation of the oscillating member 34B and results in the distal end 44B striking the casing 22, again with resultant vibration and production of sound. It will be appreciated that it would also be possible for the components to be so dimensioned that the base end 60B and distal end 44B would strike the casing simultaneously during movement of the oscillating member 34B.

In yet another construction, viewing FIG. 1C, the components are so sized that when the oscillating member 34C assumes a position at which the spring 54C is fully compressed between the head member 38C and the free end 31C of the support member 24C, the base end 60C of the stack member 40C and the distal end 44C of the field return member 36C are spaced from the casing 22. In this instance, cyclic energization of the coil 32 causes oscillation of the oscillating member 34B with resultant impact between the head member 38C, the free end 31C and the fully compressed spring 54C. The resulting vibration of the oscillating member on the support member produces the level of sound desired.

In regard to the foregoing operations, it can be said that when the coil 32 is centered on the radial magnetic field 52 produced by the oscillating member 34, it is centered on the "active region" of the field. When it is shifted over, in either direction, so that it is almost out of the radial magnetic field, it can be said to be at the edge of the active region. Now, if the annunciator 20 is being driven with pulsed DC current, its operation can be analyzed by breaking the resulting impulse into a pure DC-activated component and into a pure AC-activated component. The DC component (the average current) simply moves the oscillating member 34 against the average force of the spring 54 to place the average position of the oscillating member in the middle of the active region. The AC component can then be said to cause the oscillating member to oscillate around its average position. Variations on this mode of operation may also be considered. For example, although it may be intended to merely drive the annunciator 20 with a 50% duty cycle 30 Hz pulsed DC signal and may or may not drive it hard enough to make it impact the stops, in a manner to be described, it is also possible for the oscillating member 34 to be biased at one end of the active region and to apply huge energizing pulses to the coil 32 at very low frequencies (for example about one per second) to make it hammer the stop at the other end of the active region.

While the resilient member interposed between the oscillating member 34 and the support member 24 has been previously indicated as compression spring 54, it may take other forms and still remain within the scope of the invention. For example, viewing FIG. 5, a resilient member 62 may include elastomeric material having the proper resiliency interposed intermediate the head member 38 and the free end 31 of the support member 24.

Figure 6:
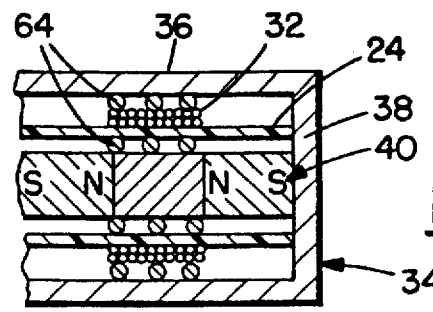
Figure 7:
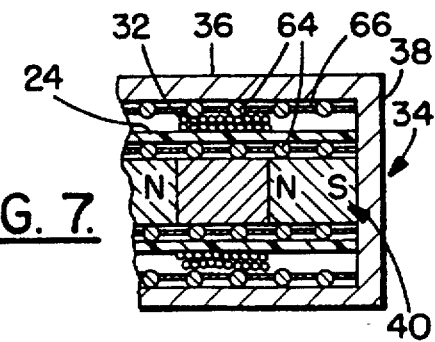

In another embodiment of the invention, viewing FIG. 6, a plurality of very small magnetically permeable balls may be interposed between the stack member 40 and the coil 32 for supporting the oscillating member for oscillation on the support member. They may also be interposed between the field return member 36 and the coil. Beneficially, they might be provided in both locations simultaneously. The magnetically permeable balls 64 are beneficial for supporting the oscillating member 34 for oscillation on the support member and they also serve to enhance the strength of the magnetic field. The magnetic field of the oscillating member is sufficiently strong to maintain the positioning of the balls so that they are coextensive with the coil 32. Nonetheless, a failsafe design may be provided as illustrated in FIG. 7 wherein a suitable retainer member 66 serves to maintain the magnetically permeable balls in position intermediate the coil 32, the stack member 40, and the field return member 36.

In yet another embodiment of the invention, viewing FIG. 8, a magnetically permeable fluid 68 such as that sold under the trademark FERROFLUID® by Ferrofluidics Corporation of Nashua, N.H. is provided intermediate at least one pair the stack member 40 and the coil 32 and the field return member 36 and the coil, respectively, for supporting the oscillating member 34 for oscillation on the support member. The magnetically permeable fluid also serves to enhance the strength of the magnetic field. As with the embodiment of FIG. 6, the magnetic field of the oscillating member 34 is sufficiently strong to maintain the positioning of the magnetically permeable fluid so that it is retained in a substantially coextensive manner with the coil 32. Nonetheless, as in the prior instance, a failsafe design is also provided in FIG. 8 wherein a suitable seal member 70 overlies the open end of the oscillating member 34 and thereby serves to prevent issuance of the magnetically permeable fluid from its interior.

Figure 9:
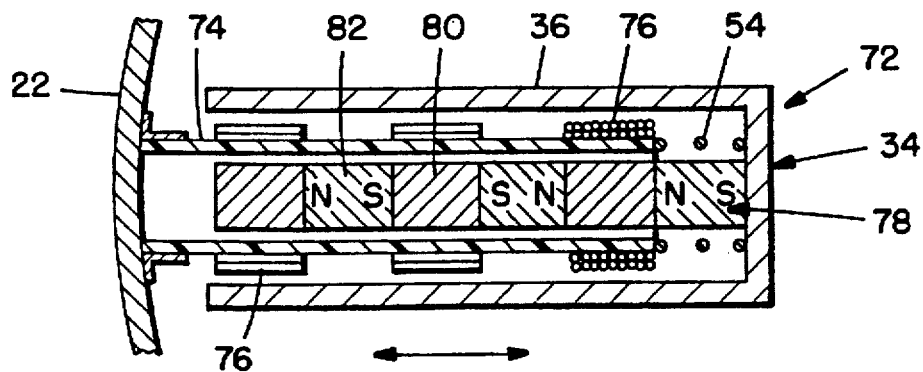

Turn now to FIG. 9 for the description of yet a further embodiment of the invention. In this instance, a modified annunciator 72 for an organ stimulating system is illustrated wherein the support member 74 is encircled by a plurality of longitudinally spaced electrically conductive coils 76. A modified stack member 78 includes a plurality of longitudinally spaced magnetically permeable pole pieces 80 and permanent magnet members 82 bonded together in a stacked relationship. Each of the pole pieces 80 corresponds to an associated one of the electrically conductive coils 76 and the associated components have substantially similar axially spacing.

In FIG. 10, another modified annunciator 84, this one being of a "pancake" design comprises a support member 86 mounted, in suitable fashion, on the casing 22 for the organ stimulating system. As in the previously described embodiments, the support member is tubular and extends to a free end 88 but is much shorter than the support member 24. Also in similar fashion, an electrically conductive coil 90 encircles the support member 86 and is bonded to the support member. An oscillating member 92 associated with the support member 86 and coil 90 includes a field return member 91 of magnetically permeable material which is spaced from and generally encircles the support member. The field return member 91 extends between a proximal end 94 and a distal end 96. A head member 98 is integral with the field return member 91 and a stack member 100 is suitably mounted on the head member and extends away therefrom toward the casing 22 for the organ stimulating system. The stack member 100 has an outer peripheral surface 102 which is spaced from the support member, the stack member including a magnetically permeable pole piece 104 and a permanent magnet member 106. The pole piece and the magnet member are in stacked relationship and together produce a radial magnetic field which extends through the coil 90 and to the field return member 91 as previously described with respect to FIG. 2. A resilient member, illustrated as being a compression spring 108, but only as an example, is positioned intermediate, and bearing against, respectively, the stack member 100 and the casing 22 of the organ stimulating system. The spring 108 serves to bias the oscillating member 92 to an initial position such that cyclic energization of the coil 90 interacts with the radial magnetic field produced by the oscillating member to cause the oscillating member to oscillate relative to the initial position.

In FIG. 11, a further modified annunciator 84A is illustrated, generally similar to the annunciator 84 but wherein a further modified support member 86A includes a plurality of longitudinally spaced electrically conductive coils 90 thereon. In this instance, a further modified stack member 100A includes the permanent magnet member 106 sandwiched between a pair of magnetically permeable pole pieces 104A, 104B, respectively. Each of the pole pieces 104A, 104B is generally coextensive with an associated one of the coils 90 when the modified oscillating member 92A is in the initial position. With the multiple-coil construction, it is necessary for modified opposed field return member 91A to be integrally connected with the further modified stack member 100A. To this end, a plurality of strut members 110 extend from the field return member 91A to the permanent magnet member 106 through slots 112 in the support member 86A to accommodate oscillating movement of the oscillating member 92A.

A structure very much similar to those already described can be used for detecting movement of a patient. Thus, as seen diagrammatically in FIG. 12, an activity sensor 120 may be encapsulated within a casing 122 and implantable in the body of a patient. The activity sensor 120 may have the construction of the annunciator 20 in FIG. 1, or in any of the other figures, as appropriate. However, for simplicity, the only components of that device illustrated in FIG. 12 are the electrically conductive coil 32 and the stack member 40. It will be appreciated that in actual fact, all of the components illustrated in FIG. 1 are intended to be present in FIG. 12. In short, the movable mass of the stack member 40 and of the oscillating member 34 of which it is a part will be affected by the motion, acceleration, or vibration of the patient and will generate a voltage across opposed leads 124, 126 and a resulting current which is received and appropriately translated by a suitable output device 128 such as an amplifier, digital to analog converter, or comparator, then to a suitable circuit 130 intended to modify pacing parameters.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An annunciator for an organ stimulating system encapsulated within a casing and implantable in the body of a patient comprising:

an elongated support member mounted at one end on the casing for the organ stimulating system, said support member being tubular and having an inner peripheral surface and extending to a free end;

an electrically conductive coil encircling said support member;

an elongated oscillating member including:
a field return member of magnetically permeable material, spaced from and generally encircling said support member, said field return member being tubular and extending between a proximal end generally proximate said free end of said support member and a distal end generally proximate the casing;

a head member integral with said field return member and overlying said proximal end thereof; and a stack member mounted on said head member and extending away therefrom toward the casing for the organ stimulating system, said stack member having an outer peripheral surface which is spaced from said inner peripheral surface of said support member;

said stack member including a magnetically permeable pole piece and a permanent magnet member, said pole piece and said magnet member being in stacked relationship which together produce a radial magnetic field which extends through said coil and to said field return member; and resilient means intermediate, and bearing against, respectively, said head member and said free end of said support member, said resilient means biasing said oscillating member to an initial position;

whereby cyclic energization of said coil interacts with said radial magnetic field to cause said oscillating member to oscillate relative to said initial position.

2. An annunciator for an organ stimulating system, as set forth in claim 1:

wherein said stack member extends to a base end at an extremity thereof;

wherein, when said oscillating member assumes said initial position, both said base end of said stack member and said distal end of said field return member are spaced from the casing; and wherein cyclic energization of said coil causing oscillation of said oscillating member results in at least one of said base end of said stack member and said distal end of said field return member to strike the casing with resultant vibration and production of sound.

3. An annunciator for an organ stimulating system, as set forth in claim 1:
   wherein said stack member extends to a base end at an extremity thereof;
   wherein, when said oscillating member assumes a position at which said resilient means is fully compressed between said head member of said oscillating member and said free end of said support member, said base end of said stack member and said distal end of said field return member are spaced from the casing; and
   wherein cyclic energization of said coil causes oscillation of said oscillating member with resultant vibration of said oscillating member on said support member and production of sound.

4. An annunciator for an organ stimulating system, as set forth in claim 1, wherein said support member, said field return member, and said stack member are all cylindrical.

5. An annunciator for an organ stimulating system, as set forth in claim 1, wherein said resilient means includes elastomeric material interposed intermediate said head member and said free end of said support member.

6. An annunciator for an organ stimulating system, as set forth in claim 1, wherein said resilient means includes a compression spring having one end engaging said head member and an opposite end engaging said free end of said support member.

7. An annunciator for an organ stimulating system, as set forth in claim 1:
   wherein said support member includes a plurality of longitudinally spaced electrically conductive coils thereon; and
   wherein said stack member includes a plurality of longitudinally spaced pairs of said magnetically permeable pole pieces and permanent magnet members, each of said pole pieces corresponding to each of said electrically conductive coils and having substantially similar axial spacing.

8. An annunciator for an organ stimulating system encapsulated within a casing and implantable in the body of a patient comprising:
   a support member mounted on the casing for the organ stimulating system, said support member being hollow and having an inner peripheral surface defining a cavity therein, said support member extending to a free end;
   an electrically conductive coil encircling said support member;
   a hollow oscillating member including: a field return member of magnetically permeable material slidably engaged with and generally enveloping said support member, said oscillating member extending between a distal end generally proximate the casing and a base end generally proximate said free end of said support member;
   a stack member mounted on said oscillating member and extending through the cavity of said support member toward the casing for the organ stimulating system, said stack member having an outer peripheral surface which is slidably engaged with said inner peripheral surface of said support member;
   said stack member including a first magnetically permeable member and a second permanent magnet member, said first and second members being in stacked relationship which together produce a radial magnetic field which extends through said coil and to said field return member;
   a resilient member intermediate said oscillating member and said free end of said support member biasing said oscillating member to an initial position; and
   whereby cyclic energization of said coil interacts with said radial magnetic field to cause said oscillating member to oscillate relative to said initial position.

9. An annunciator for an organ stimulating system encapsulated within a casing and implantable in the body of a patient comprising:
   oscillating means including a head member, a tubular magnetically permeable outer wall member extending from said head member to a free end at an extremity thereof, and a central elongated stack member mounted on said head member and extending to a base end, said outer wall member and said central stack member defining an annular cavity therebetween, said stack member including an magnetically permeable member and a permanent magnet member in back-to-back relationship;
   electrically conductive coil means mounted on and electrically insulated from the casing and slidably received in the annular cavity of said oscillating means and slidably engaged with said outer wall member and with said stack member;
   resilient means intermediate, and bearing against, said head member and said coil means biasing said oscillating means to a first position whereat said base end and said free end are spaced from the casing; and
   whereby cyclic energization of said coil means creates a magnetic field which interacts with the magnetic field produced by said stack member to move said oscillating means axially such that at least one of said base end and said free end strikes the casing creating noise and vibration of the casing.

* * * * *